United States Patent
López Del Pueyo et al.

(10) Patent No.: US 12,108,973 B2
(45) Date of Patent: Oct. 8, 2024

(54) BONE CLAMP

(71) Applicant: CYBER SURGERY, S.L., Guipúzcoa (ES)

(72) Inventors: Javier López Del Pueyo, San Sebastián (ES); Álvaro Escudero Martínez De Ibarreta, San Sebastián (ES); Anne Fernández Lopo, San Sebastián (ES); Laurentzi Garmendia Iartza, San Sebastián (ES); Andrés Amarillo Espitia, San Sebastián (ES); Ainitze Mendizabal Dones, San Sebastián (ES)

(73) Assignee: CYBER SURGERY, S.L., Guipuzcoa (ES)

( * ) Notice: Subject to any disclaimer, the term of this patent is extended or adjusted under 35 U.S.C. 154(b) by 435 days.

(21) Appl. No.: 17/451,702

(22) Filed: Oct. 21, 2021

(65) Prior Publication Data
US 2022/0125496 A1    Apr. 28, 2022

(30) Foreign Application Priority Data
Oct. 22, 2020   (EP) ..................... 20382920

(51) Int. Cl.
*A61B 17/28*   (2006.01)
*A61B 17/88*   (2006.01)

(52) U.S. Cl.
CPC ...... *A61B 17/8866* (2013.01); *A61B 17/2804* (2013.01); *A61B 2017/2808* (2013.01)

(58) Field of Classification Search
CPC .................................................. A61B 17/8866
See application file for complete search history.

(56) References Cited

U.S. PATENT DOCUMENTS

| | | | | |
|---|---|---|---|---|
| 1,985,108 A | * | 12/1934 | Rush ............... | A61B 17/8866 606/86 R |
| 2,181,746 A | * | 11/1939 | Siebrandt ......... | A61B 17/282 7/125 |
| 2,362,957 A | * | 11/1944 | Hackett ........... | A61B 17/8861 606/86 R |
| 2,427,128 A | * | 9/1947 | Ettinger .......... | A61B 17/8866 606/86 R |

(Continued)

FOREIGN PATENT DOCUMENTS

| | | |
|---|---|---|
| DE | 20 2006 019649 U1 | 8/2007 |
| EP | 1967155 A1 | 9/2008 |

(Continued)

OTHER PUBLICATIONS

European Search Report issued in the counterpart EP20382920.5, dated Apr. 19, 2021 in 9 pages.

*Primary Examiner* — Nicholas W Woodall
(74) *Attorney, Agent, or Firm* — Knobbe, Martens, Olson & Bear, LLP

(57) ABSTRACT

The present disclosure is related to surgical devices, more particular it refers to a surgical clamp that attaches to a patient's bone to assist in surgical procedures. The surgical clamp is configured in such a manner that the clamping elements show a movement in a plane different from the plane of the actuator intended for opening and closing said clamping elements. As a result, the surgical clamp provides a broader working space to the surgeon when carrying out surgical work on the spine.

20 Claims, 5 Drawing Sheets

(56) References Cited

U.S. PATENT DOCUMENTS

| | | | |
|---|---|---|---|
| 2005/0049629 A1* | 3/2005 | Koo | A61B 17/8866 606/201 |
| 2007/0162031 A1* | 7/2007 | Hogg | A61B 17/8866 606/79 |
| 2007/0244516 A1* | 10/2007 | Chiu | A61B 17/326 606/207 |
| 2009/0024127 A1* | 1/2009 | Lechner | A61B 90/39 606/53 |
| 2011/0004259 A1* | 1/2011 | Stallings | A61B 90/39 606/86 R |
| 2014/0378998 A1* | 12/2014 | Rizzuto | A61B 34/30 606/130 |
| 2016/0242800 A1* | 8/2016 | Melsheimer | A61B 17/3201 |
| 2017/0281283 A1 | 10/2017 | Siegler et al. | |

FOREIGN PATENT DOCUMENTS

| | | |
|---|---|---|
| EP | 3494903 A1 | 6/2019 |
| EP | 3622913 A1 | 3/2020 |

* cited by examiner

BONE CLAMP

CROSS-REFERENCE TO RELATED APPLICATIONS

This application claims priority to European Patent Application No. EP20382920.5 filed on Oct. 22, 2020, which is hereby incorporated by reference and made a part of this specification.

BACKGROUND

Field

The present disclosure is related to surgical devices, more particular it refers to a surgical clamp that attaches to a patient's bone to assist in surgical procedures. The surgical clamp is configured in such a manner that the clamping elements show a movement in a plane different from the plane of the actuator intended for opening and closing said clamping elements. As a result, the surgical clamp provides a broader working space to the surgeon when carrying out surgical work on the spine.

Description of Related Art

Surgical procedures on a patient's bone, such as spine, usually require the use of specific surgical devices such as clamps to fix or hold reference elements or auxiliary devices to the bone to be intervened on.

In some specific applications, the clamp is attached to a predetermined vertebra and comprises reference elements that are intended to be reference elements located within the observable space of a plurality of cameras. A computer system receives the images captured by the plurality of cameras and is adapted to determine the correct location and orientation of the vertebra in view of the observed locations of the reference elements.

These clamps, in some other specific applications are connected or linked to tracking systems so that it serves as an anchor reference for tracking systems in a surgery procedure.

Conventionally, in any of the identified contexts, the bone clamps have a clamp opening and closing mechanism for attaching the clamp to the bone to be intervened.

The camp device has two jaws with at least one jaw movable in respect to the other jaw. A first jaw is attached to one side of the spine and the other jaw is attached to the opposite side of the spine wherein the movement of the two jaws during the clamping process occurs mainly according to a plane perpendicular to the spine.

The opening and closing mechanism is based on some prolongations of each jaw that are actuated by the user and therefore they also show movements in the same perpendicular plane to the spine.

Even if the shape of the clamp is very compact, in the open position and in the closed position of the clamp, the shape of clamp requires that some of its parts, in particular the prolongations of the opening mechanism, invade a certain space on either side of the spine.

The main actuations of surgeons on the spine are at one side of the spine and therefore the opening and closing mechanisms reduces the available space for the surgery.

Therefore, there is a need in the art for improved devices showing a stable fixation to the patient's bone in a surgery procedure while facilitating the positioning of these devices and their fixation without getting in the way of surgery procedure on patient's spine.

SUMMARY

The present disclosure provides a solution for the aforementioned problems. Through claims, preferred embodiments, and drawings, the disclosures are explained.

In a first aspect, the disclosure provides a bone clamp comprising:
- a main body comprising at one end a first jaw,
- a second jaw rotationally connected to the main body and being opposite of the first jaw, the second jaw comprising at least an open jaw position and closed jaw position so that both first and second jaws define a grip portion, and
- an actuator configured for opening and closing the second jaw, the actuator being rotationally connected to the main body and comprising at least an open actuator position and a closed actuator position, wherein
the actuator and the second jaw are linked by a kinematic chain so that the passage of the actuator from one actuator position to another actuator position causes the second jaw to pass from one jaw position to another jaw position respectively, and
the rotational movement of the actuator is contained in a first plane and the rotational movement of the second jaw is contained in a second plane wherein the orientation of the first plane and the orientation of the second plane are different.

The present bone clamp is a surgical clamp intended to be attached to a bone of a patient, e.g., a spine, in a surgical procedure. Particularly, the clamp is fixed on the patient's bone in an area close to where a surgical intervention is to be performed. This clamp, once attached to the bone, can be used as a reference component for the bone to be intervened on, so that the bone clamp can be connected to a fiducial element or to a mechanical tracker in a surgical system for a surgical intervention.

A reference component must be interpreted as a component that, once it has been fixed to the bone, the bone and the reference component have a movement as they are a single body and, therefore, the movement of the reference can be interpreted as the movement of the bone mainly when the bone is not visually accessible.

The bone clamp comprises a main body preferably shaped like an elongated rod extending outward the patient's bone when the clamp is fixed to said bone. The main body will be understood as a rigid body.

The bone clamp further comprises two jaws, a first jaw and a second jaw, that allow fixing this clamp to a patient's bone. Particularly, the first jaw is comprised on the main body and is located in one of the ends of the main body. The second jaw is an independent component from the main body but it is connected to this. Specifically, the second jaw is rotationally connected to the main body close to the end of the main body where the first jaw is placed so that the second jaw is opposite to the first jaw.

This second jaw defines at least two jaw positions, an open jaw position and a closed jaw position. The fact that both jaws are opposite between them and the second jaw comprises the mentioned two jaw positions, both first and second jaw defines a grip portion in the bone clamp. That is, the fixing of the clamp to a bone is provided at the grip portion and thanks to both jaws.

The bone clamp also comprises an actuator for opening and closing the second jaw relative to the first jaw, that is, the actuator controls the gripper of the clamp by opening and closing this second jaw with respect to the first jaw. This gripper will be understood as the attachment or adherence of the clamp jaws, for example, relative to a bone surface of a patient. The actuator is also rotationally connected to the main body as well as the second jaw. That is, the actuator actuates an open and a closed jaw positions in the second jaw and comprises at least an open actuator position and a closed actuator position.

The actuation of the actuator is linked with the rotational movement of the second jaw relative to the main body so that the gripper of the clamp can be regulated. In particular, the link between the actuator and the second jaw is provided by a kinematic chain. In this sense, the passage of the actuator from one actuator position to another actuator position causes the second jaw to pass from one jaw position to another jaw position respectively. In addition, the rotational movement of the actuator relative to the main body is contained in a first plane with a different orientation than a second plane where the rotational movement of the second jaw relative to the main body is contained.

Advantageously, the present disclosure provides an improved clamp with a configuration that ensures fixation to a patient's bone in a surgical intervention and is a clamp easy to actuate. Furthermore, the present bone clamp facilitates the manipulation of the patient's bone to be intervened since the clamp actuation is performed from a plane that does not intervene in the surgical intervention region.

In operative manner, the plane of the grip portion comprising the first jaw and the second jaw is perpendicular to the spine since the two jaws are intended for clamping the spinous apophysis. As a result, the rotational movement of the actuator is different to the plane defined by the movement of the two jaws and therefore the actuator does not invade the working space of the surgeon.

According to an embodiment, the second plane (P2) and the first plane (P1) has an angle in the range [60°, 120°], more preferably in the range [70°, 110°], more preferably in the range [80°, 110°].

In a particular embodiment, the second plane is perpendicular to the first plane.

That is, the rotational movement performed by the actuator relative to the main body is perpendicular to the rotational movement of the second jaw also relative to the main body. This perpendicular configuration between planes, advantageously, ensure that the actuation of the bone clamp does not intervene in a surgical intervention region of the bone where the clamp is fixed according to optimal conditions.

In a particular embodiment, the kinematic chain is partially housed within the main body, the actuator pivots in a first joint of the main body and the second jaw pivots in a second joint of the main body by means of the rotation of the actuator, the second joint being separated from the first joint.

The main body, according to a preferred embodiment, is a hollow body for allowing to house part of the kinematic chain that links the actuator to the second jaw. The actuator pivots in a first joint of the main body and second jaw pivots in a second joint of the main body, this second joint being separated from the first joint. These two first and second joints form part of the kinematic chain. In this sense, the rotation of the actuator in the first joint of the main body causes the rotation of the second jaw in the second joint of the main body. That is, the rotation of the second jaw is a consequence of the actuator rotation whilst the first jaw remains fixed since it is part of the rigid main body.

In a particular embodiment, the kinematic chain comprises:
  a slider, and
  a first and second rod-cranks,
wherein the kinematic chain is adapted to transform the rotational movement of the actuator to a linear displacement of the slider by means of the first rod-crank rotatably connecting the actuator and the slider, and subsequently to transform the linear displacement of the slider to the rotational movement of the second jaw by means of the second rod-crank rotatably connecting the slider and the second jaw.

In order to cause the rotational movement of the second jaw through the rotational movement of the actuator, the kinematic chain transform the rotational movement of the actuator to the rotational movement of the second jaw by means of a slider and two rod-cranks. Particularly, the kinematic chain comprises a first rod-crank which rotatable connects the actuator and the slider so that this first rod-crank transforms the rotational movement of the actuator into a linear displacement of the slider. Further, the kinematic chain comprises a second rod-crank which rotatable connects the slider and the second jaw so that this second rod-crank transforms the linear displacement of the slider causes by the first rod-crank into the rotational movement of the second jaw. The actuation of the second rod-crank is subsequent to the actuation of the first rod-crank, and the slider is forced to acquire a linear motion since it is guided inside the main body. Advantageously, the kinematic chain facilitates the movement transmission between the actuator and the second jaw in the bone clamp by means of movement's transformation.

In a more particular embodiment, when the bone clamp is in operative mode, the first rod-crank movement is in the first plane and, in operative mode, the second rod-crank movement is in the second plane.

According to this specific embodiment, the slider is the element allowing to combine two different orientations according to two different planes of movement since the linear displacement does not depend on any orientation.

More particularly, the actuator is connected to the first rod-crank by means of an extension arm extending the actuator to an opposite side of a first joint about which the actuator rotates, so that the opening of the actuator causes the second jaw to open.

This extension arm is part of the kinematic chain and is an extension of the actuator from the first joint of the main body where the actuator pivots to an opposite side of this first joint where connects to the first rod-crank. This configuration transforms the opening of the actuator into the opening of the second jaw relative to the main body.

In another particular embodiment, the actuator is directly connected to the first rod-crank so that the opening of the actuator causes the second jaw to close.

This configuration transforms the opening of the actuator into the closing of the second jaw relative to the main body.

In a particular embodiment, the bone clamp further comprises an actuator movement regulation mechanism comprising a locked position where the actuator is fixed and a free position where the actuator can rotate.

This mechanism regulates the rotational movement of the actuator so that is able to fix the actuator and allow the rotation of the actuator. When the actuator is fixed and cannot rotate the mechanism is in a lock position whilst when then actuator can rotate the mechanism is in a free position. Advantageously, this actuator movement regulation mechanism allows controlling the gripper of the clamp by means of the second jaw rotation.

In a more particular embodiment, the actuator movement regulation mechanism is a ratchet mechanism and comprises at least:
- an arc-shaped rack protruding from the main body and comprising a plurality of teeth, and
- a pawl rotationally connected to the actuator and comprising at least a tooth that matches those teeth of the arc-shaped rack, wherein
in the free position of the mechanism the pawl is configured to rotate with respect to the actuator and to slide through the arc-shaped rack thus allowing the actuator to rotate with respect to the arc-shaped rack, and
in the locked position the pawl movement remains blocked so that the actuator remains fixed.

The mechanism is understood as a ratchet mechanism and comprises an arc-shaped rack and a pawl. According to an embodiment, this arc-shaped rack is a circular rack that protrudes from the main body and is parallel to the first plane containing the rotational movement of the actuator. The arc-shaped rack comprises in its upper portion a toothed surface with a plurality of teeth. The pawl is rotationally connected to the actuator and comprises at least a tooth adapted to match and be locked into the toothed surface of the arc-shaped rack.

When the mechanism is in the free position, the pawl rotates with respect to the actuator and slide through the arc-shaped rack so that the actuator rotates with respect to the arc-shaped rack along the toothed surface of this rack. On the other hand, when the mechanism is in the lock position, the movement of the pawl is blocked and the actuator remains fixed.

In a more particular embodiment, the ratchet mechanism further comprises a spring element attached to the actuator and arranged to apply a force to the pawl thus ensuring the contact of the tooth of the pawl with the teeth of the arc-shaped rack.

The pawl is configured to keep the locked position once the pawl is engaged into the toothed surface; nonetheless, according to this embodiment the spring element ensures a force for ensuring the contact and therefore this configuration reduces the uncertainty associated to the security level of the locking mechanism.

In another particular embodiment, the ratchet mechanism further comprises a security handle protruding from the actuator and configured to lock the movement of the pawl in the locked position of the mechanism.

This handle ensure blocking the movement of the pawl in the lock position of the mechanism.

In a particular embodiment, the clamp further comprises a kinematic coupling connected to the main body in an end opposite to the first jaw, the kinematic coupling being configured to be coupled to tracking means so that the bone clamp provides an anchor reference.

This kinematic coupling in an end of the main body attaches the bone clamp to an external element (such as a fiducial element or the mechanical tracker) and allows the bone clamp to be an anchor reference for tracking means since it ensures that the movement of the kinematic coupling is the movement of the bone like of both bodies are the same body.

In a more particular embodiment, the kinematic coupling comprises:
- a female portion comprising a ferromagnetic element, and and a male portion comprising at least a magnet, wherein the ferromagnetic element and the at least magnet provide a bonding force between both female and male portions.

The kinematic coupling, as already mentioned, is adapted to join the present bone clamp to either a fiducial element or mechanical tracker. Either way, both female and male parts comprised in the kinematic coupling are composed by the same elements. Particularly, the kinematic coupling provides a bonding force between the female and male portions thanks to a ferromagnetic element and a magnet of the female and male respectively.

In a more particular embodiment, the female portion further comprises three grooves forming at least six planes and the male portion further comprises three spheres or semi-spheres and a set of magnets. These spheres of the male portion are configured to match with the grooves of the female portion providing a unique position and orientation of matching. Each sphere of the male portion contacts with two planes formed by a groove of the female portion so that the kinematic coupling provides six contact forces. This contact forces advantageously ensures the unique coupling between female and male portions with no looseness and the ferromagnetic element of the female portion and the magnets of the male portion ensure the bonding force between both portions in the kinematic coupling.

In addition, the overall profile of the female portion comprises a ledge suitable to ease the manual coupling operation in the kinematic coupling, and the overall profile of the male portion comprises an opening configured to fit into the ledge to further ensure the correct coupling between both portions of the kinematic coupling.

In a particular embodiment, the first and second jaw comprises a plurality of spikes so that in the closed jaw position the spikes of both first and second jaw are facing each other.

The provision of spikes in both jaws improve the gripping and ensure the fixing of the clamp to a patient's bone since the spikes are driven into the bone improving fixation.

BRIEF DESCRIPTION OF THE DRAWINGS

These and other features and advantages of the disclosure will be seen more clearly from the following detailed description of a preferred embodiment provided only by way of illustrative and non-limiting example in reference to the attached drawings.

DETAILED DESCRIPTION

Figure 1:
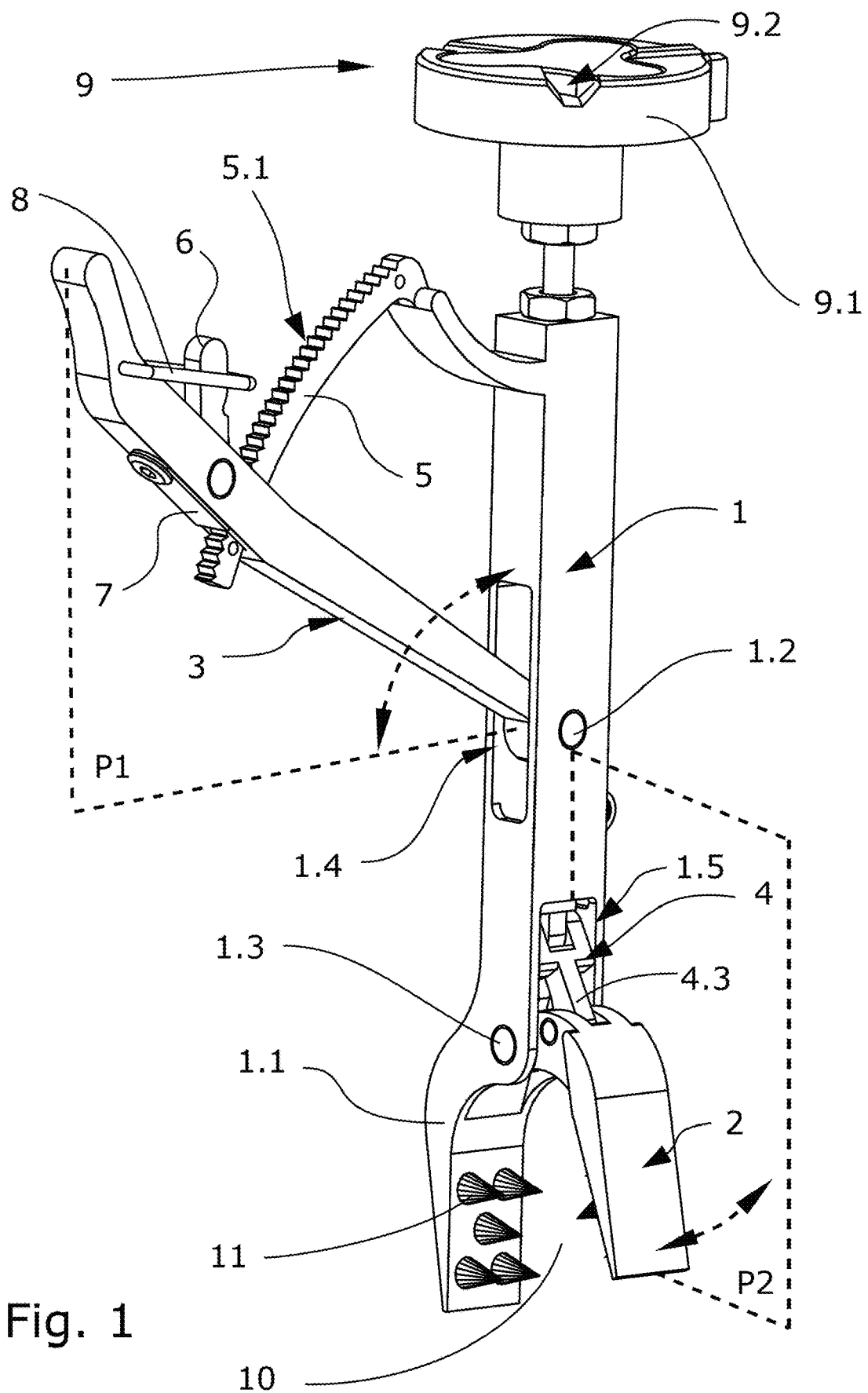
FIG. 1 This figure shows a perspective view of a bone clamp in a first position according to an embodiment of the present disclosure.
Figure 2:
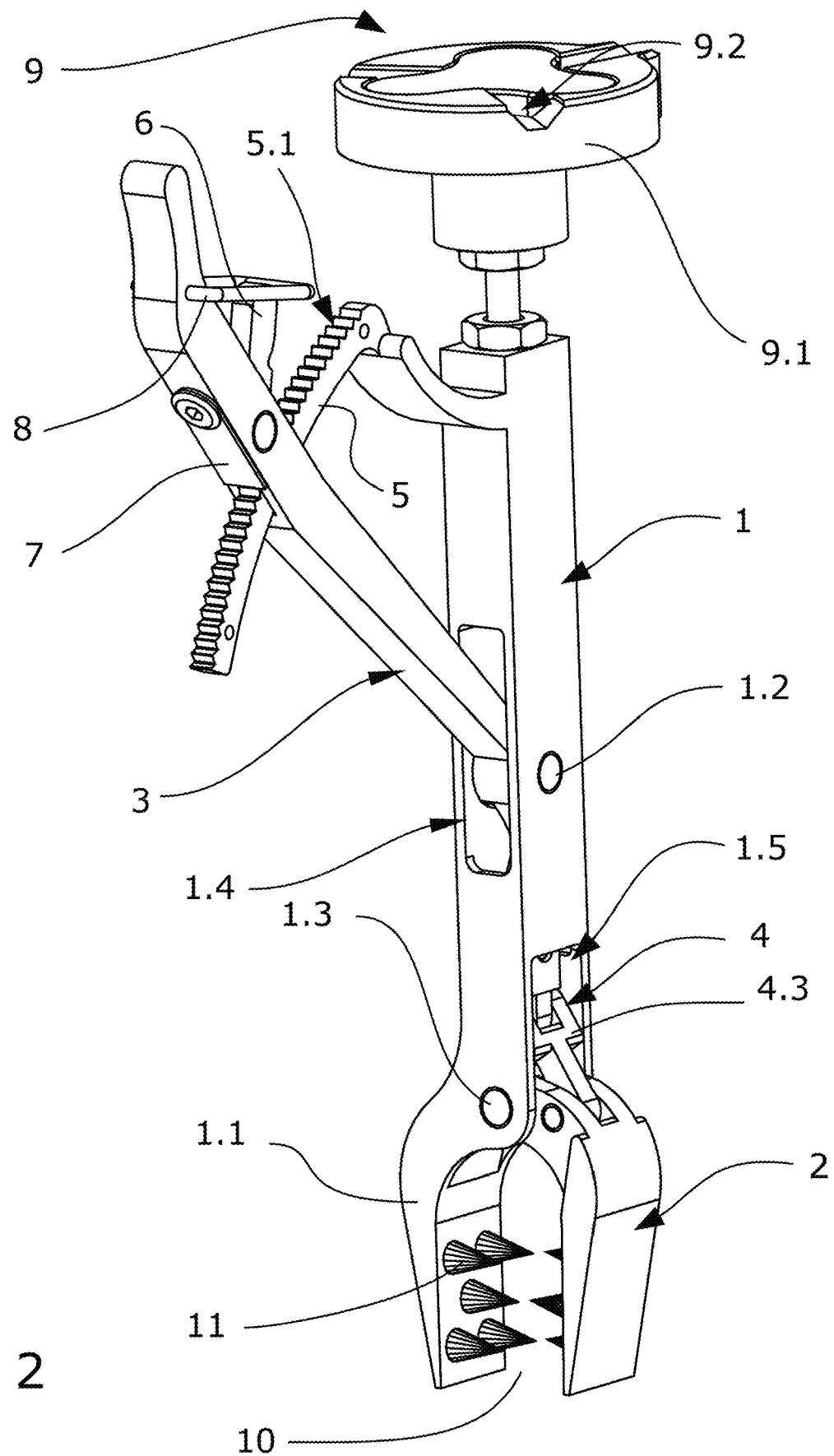
FIG. 2 This figure shows a perspective view of a bone clamp in a second position according to an embodiment of the present disclosure.
Figure 3:
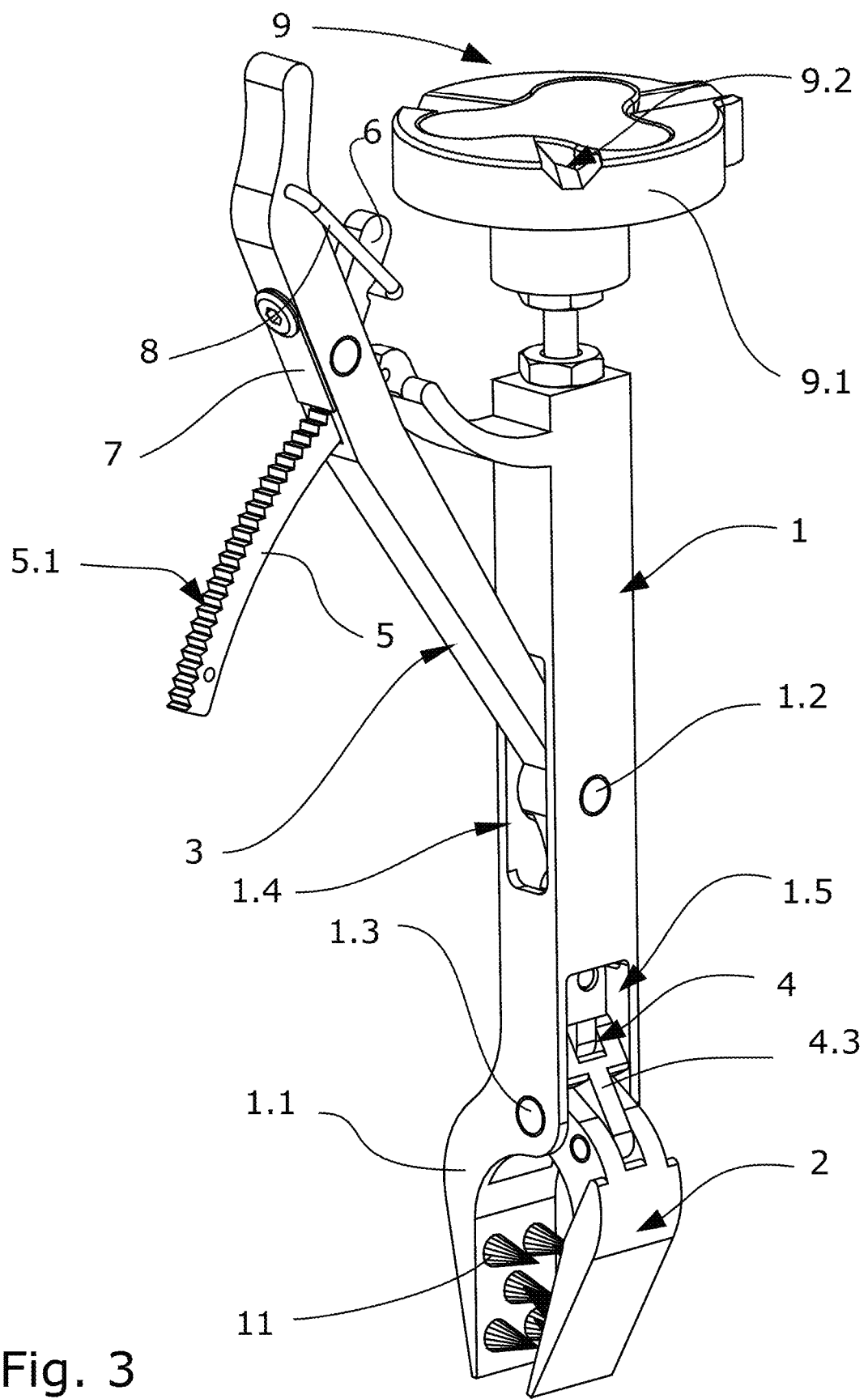
FIG. 3 This figure shows a perspective view of a bone clamp in a third position according to an embodiment of the present disclosure.

FIGS. 1-3 show an embodiment of the present bone clamp in different positions. This bone clamp comprises a main body (1) as an elongated structure that is hollow inside at least in a portion of the body. The main body (1) comprises in one of its ends a first jaw (1.1) with a plurality of spikes (11) arranged on a surface of this first jaw (1.1).

The bone clamp further comprises a second jaw (2) that is rotationally connected to the main body (1) at a joint that will be identified as second joint (1.3) and, is opposite of the first jaw (1.1). This second jaw (2) also comprises a plurality of spikes (11) on a surface of this second jaw (2) so that the spikes (11) of the second jaw (2) are faced to the spikes (11) of the first jaw (1.1).

The second jaw (2) comprises at least an open jaw position and a closed jaw position wherein both first (1.1) and second (2) jaws define a grip portion (10). The open jaw position defines a greater aperture in the grip portion (10) than the closed jaw position. Both first (1.1) and second (2) jaw are intended to grip a patient's bone when the second jaw (2) is in its closed jaw position.

In addition, the bone clamp comprises an actuator (3) configured for opening and closing the grip portion (10) by moving the second jaw (2), that is, through the rotation of this second jaw (2) with respect to the main body (1) at the second joint (1.3). The actuator (3) is rotationally connected to the main body (1) at a first joint (1.2) that is separated along said main body (1) from the second joint (1.3). Moreover, the actuator (3) comprises at least an open actuator position and a closed actuator position.

The actuator (3) and the second jaw (2) are linked by a kinematic chain (4) that is partially housed within the main body (1). This kinematic chain (4) allows that the passage of the actuator (3) from one actuator position to another actuator position causes the second jaw (2) to pass from one jaw position to another jaw position respectively.

Specifically, FIG. 1 shows a bone clamp with a second jaw (2) in an open jaw position being actuated by the actuator (3) in its open actuator position. On the other hand, FIG. 3 shows a bone clamp with a second jaw (2) in a closed jaw position actuated by the actuator (3) in its closed actuator positions. Particularly, FIG. 2 shows a bone clamp position that is a transition between the position of FIGS. 1 and 3 and vice versa.

Therefore, the kinematic chain (4) is in charge of transforming the rotational movement of the actuator (3) into the rotational movement of the second jaw (2) for opening or closing this second jaw (2) relative to the first jaw (1.1). Particularly, the rotational movement of the actuator (3) is contained in a first plane (P1) that is different to a second plane (P2) where the rotational movement of the second jaw (2) is contained, that is, the orientation of these first and second plane (P1, P2) is different between them. In the particular example shown on FIGS. 1 to 3, these first and second planes (P1, P2) are orthogonal between them. As a result of this orthogonal condition, since the first joint (1.2) and the second joint (1.3) are in the form of shafts allowing the rotation of the actuator (3) and the second jaw (2) respectively, the axis of said shafts are also orthogonal. The first plane (P1) and the second plane (P2) along with a double arrow using dashed lines indicating the movement are schematically shown only in FIG. 1 in order to avoid too many lines close to other relevant elements in the sake of clarity.

According to this specific embodiment, the actuator (3) pivots inside the main body (1) at the first joint (1.2) and is partially housed within the main body (1) so that the actuator (3) penetrates the main body (1) through a first opening (1.4). On the other hand, the second jaw (2) pivots inside the main body (1) at the second joint (1.3) and is partially housed within the main body (1) through a second opening (1.5) in the main body (1). This second opening (1.5) is arranged in a side of the main body (1) that is perpendicular to the side where the first opening (1.4) is located.

The main body (1) further comprises a third opening (not shown in figures) that is arranged in a side of the main body (1) that is opposite to the side where the first opening (1.4) is located and perpendicular to the side where the second opening (1.5) is located. This third opening allows part of the kinematic chain (4) protrudes towards outside the main body (1) when needed.

The kinematic chain (4) transforms the rotational movement of the actuator (3) performed in the first plane (P1) into the rotational movement of the second jaw (2) performed in the second plane (P2). Both rotational movements of the actuator (3) and second jaw (2) respectively are performed with respect to the main body (1) in different joint points.

The present bone clamp shown on FIGS. 1-3 further comprises a mechanism for regulating the movement of the actuator (3). This actuator movement regulation mechanism defines a locked position where the actuator (3) is fixed in one of these positions and a free position if the actuator (3) can rotate on the first joint point (1.2) with respect to the main body (1).

Particularly, this mechanism is a ratchet mechanism that comprises on one hand an arc-shaped rack (5) and a pawl (6). The arc-shaped rack (5) is a circular rack that protrudes from the main body (1) and forms part of this main body (1). The arc-shaped rack (5) comprises a plurality of teeth along the upper surface of this rack (5). According to this embodiment, the actuator (3) is perforated defining a hole through which the arc-shaped rack (5) passes. The pawl (6) is rotationally connected to the actuator (3) and comprises at least a tooth that matches those (5.1) teeth of the arc-shaped rack (5).

When the ratchet mechanism is in its free position, the pawl (6) can rotate with respect to the actuator (3) for sliding through the circular portion of the arc-shaped rack (5) thus allowing the actuator (3) to rotate. In particular, the ratchet mechanism also comprises a spring element (7) that is attached to the actuator (3) and is adapted to apply a force to the pawl (6) to ensure the contact of the tooth of the pawl (6) with the teeth (5.1) of the arc-shaped rack (5). In an example, the spring element (7) is an elastically deformable flat metal piece, preferably by using a thin plate that is attached to the actuator (3) by a screw. This spring element (7) is flexible.

On the other hand, when the ratchet mechanism is in its locked position, the pawl (6) movement remains blocked by means of a security handle (8) protruding from the actuator (3), so that the actuator (3) remains fixed at an actuator position.

In this sense, FIGS. 1-3 show different positions of the actuator (3) with respect to the circular rack (5). In FIGS. 1 and 3, the ratchet mechanism is in a locked position remaining the actuator (3) fixed in an open and closed position respectively, whilst in FIG. 2 the ratchet mechanism is in a free position allowing the actuator (3) to rotate. Both FIGS. 1 and 3 show the security handle (8) holding the pawl (6) for ensuring the fixation of the actuator (3) and avoiding the tooth of the pawl (6) slide along with the teeth (5.1) of the arc-shaped rack (5). However, FIG. 2 shows how the security handle (8) does not hold the pawl (6) and it is allowed the movement of the actuator (3) along with the circular rack (5).

The pawl (6), according to this embodiment, shows a recess adapted to receive the security handle in a locked position.

The bone clamp shown on FIGS. 1-3 further comprises a kinematic coupling (9) connected in an end of the main body (1) that is opposite to the end where the first jaw (1.1) is located. This kinematic coupling (9) is configured to be coupled to tracking means so that the bone clamp provides an anchor reference. Specifically, the kinematic coupling (9) comprises a female portion (9.1) and a male portion (not shown). The female portion (9.1) comprises a ferromagnetic element that is attracted to a magnet located on the male portion. In this way, both the ferromagnetic element of the female portion (9.1) and the magnet of the male portion provide a bonding force between the female and male portions.

According to another embodiment, the ferromagnetic element is in the male portion and the magnet is in the female portion (9.1) ensuring the bonding force between said female and male portions.

In the example shown on FIGS. 1-3, the female portion (9.1) of the kinematic coupling (9) has three machined grooves (9.2) that form at least six inclined planes suitable for receiving three spheres or semi-spheres and comprised in the male portion (not shown). This male portion has a set of magnets distributed along with it for contacting with the ferromagnetic element of the female portion (9.1). Particularly, these spheres of the male portion match with the grooves (9.2) of the female portion (9.1) in a unique position and orientation. So that, each sphere contact with two incline planes of the female portion (9.1) for providing three locations through the six points of contact ensuring the unique coupling in the kinematic coupling (9). The ferromagnetic element of the female portion (9.1) and the magnets of the male portion ensure the bonding force between both positions of the kinematic coupling (9).

Figure 4:
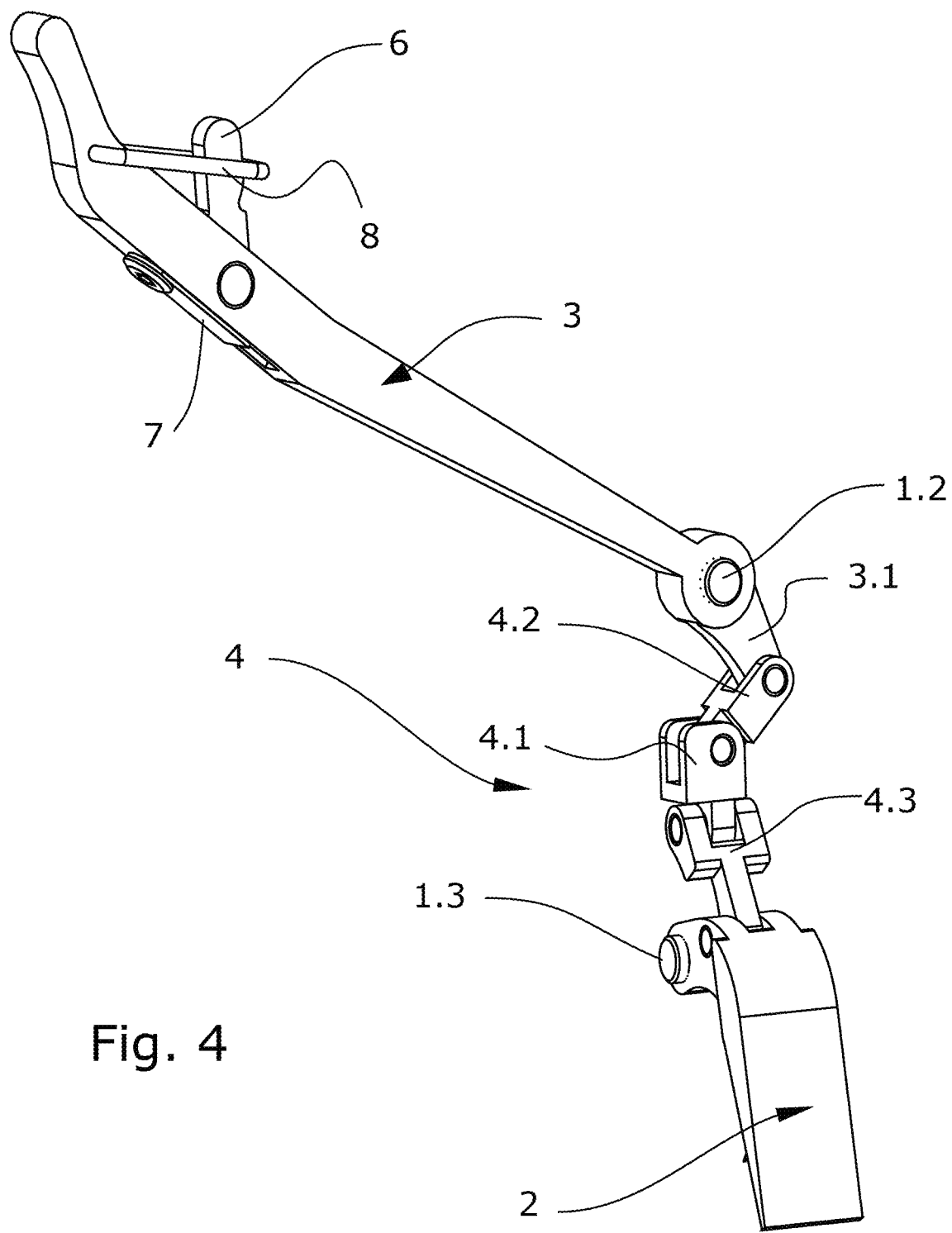
FIG. 4 This figure shows a perspective view of a movable portion of the bone clamp in a first position according to an embodiment of the present disclosure.
Figure 5:
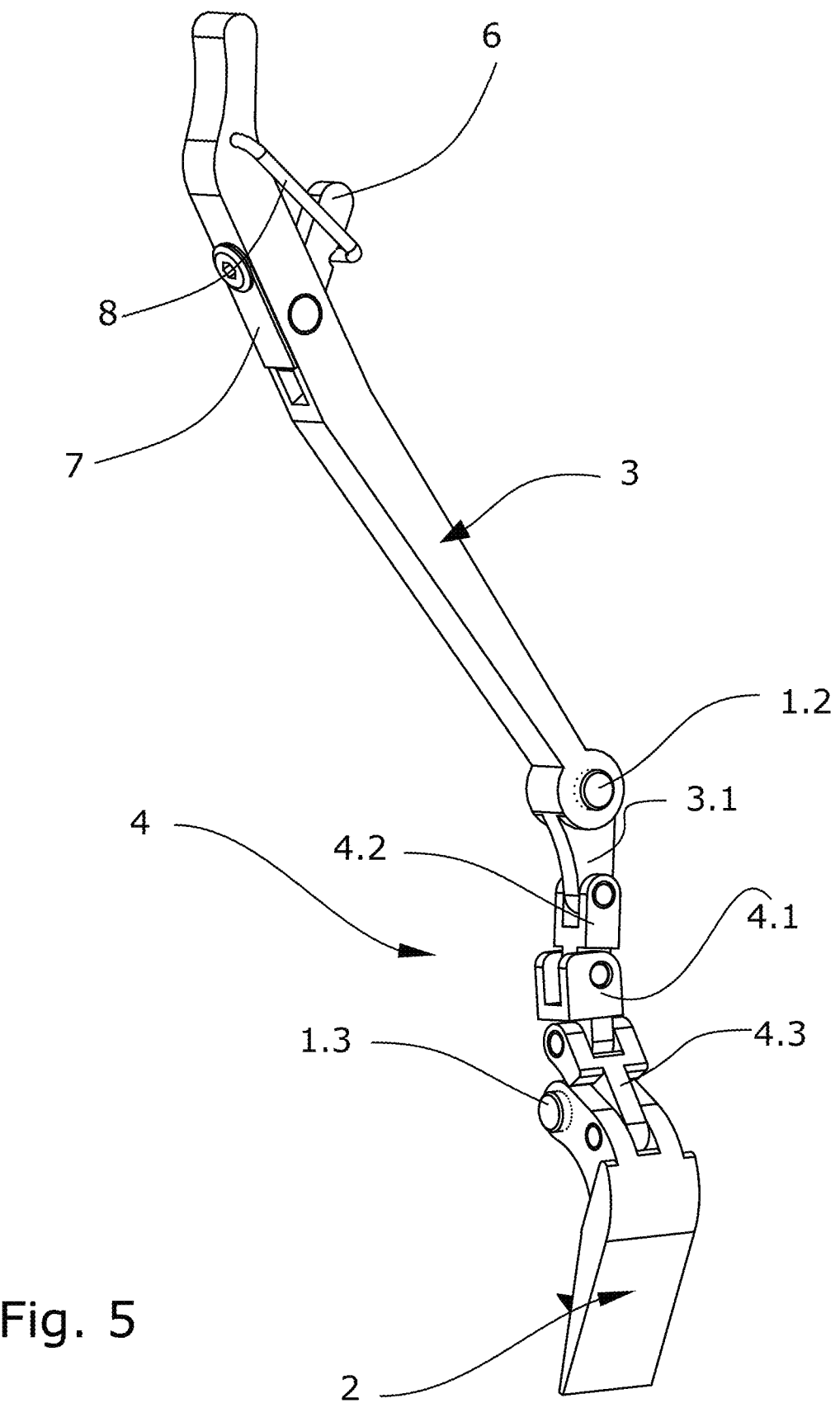
FIG. 5 This figure shows the movable portion of FIG. 4 in a second positon according to an embodiment of the present disclosure.

The kinematic chain (4) of the bone clamp shown on FIGS. 1-3 is shown in detailed on FIGS. 4 and 5. These FIGS. 4 and 5 show que joint between the actuator (3), the kinematic chain (4) and the second jaw (2) without showing the main body (1) that would hide some inner parts in order to observe in detail the configuration of the kinematic chain (4). The kinematic chain (4) shown in these figures comprises a slider (4.1) and two rod-cranks (4.2, 4.3).

In these FIGS. 4 and 5, the actuator (3) is connected to a first rod-crank (4.2) by means of an extension arm (3.1) extending the actuator (3) at an opposite side of the first joint (1.2) about which the actuator (3) rotates, so that the opening of the actuator (3) causes the second jaw (2) to open. The first rod-crank (4.2) is rotatably connecting the actuator (3) and the slider (4.1). In another example, the actuator (3) can be directly connected to the first rod-crank (4.2) rather than using an extension arm (3.1) so that the opening of the actuator (3) causes the second jaw (2) to close.

The second jaw (2) is connected to a second rod-crank (4.3) that is rotatably connected to the slider (4.1) and this second jaw (2).

In operative mode, the first rod-crank (4.2) movement of the kinematic chain (4) is in the first plane (P1) where the rotational movement of the actuator (3) is contained. Furthermore, in operative mode, the second rod-crank (4.3) movement is in the second plane (P2) where the rotational movement of the second jaw (2) is contained.

In order of performance, the rotational movement of the actuator (3) in the first joint (1.2) is transformed to a linear displacement of the slider (4.1) by means of the first rod-crank (4.2), and subsequently, the linear displacement of the slider (4.1) is transformed to a rotational movement of the second jaw (2) in the second joint (1.3) by means of the second rod-crank (4.3). Therefore, the kinematic chain (4) provides the actuation of the second jaw (2) through the actuation of the actuator (3).

The slider (4.1) is housed in the main body (1) wherein the shape of the housing is configured for being a linear guide of the linear movement of the slider (4.1).

FIG. 4 particularly shows the position of the components of the kinematic chain (4) when the bone clamp is in the position shown on FIG. 1. By contrast, FIG. 5 shows the position of the components of the kinematic chain (4) when the bone clamp is in the position shown on FIG. 3.

What is claimed is:

1. Bone clamp comprising:
    a main body comprising at one end a first jaw, the main body and the first jaw forming a single rigid body;
    a second jaw rotationally connected to the main body and being opposite of the first jaw, the second jaw comprising an open jaw position and closed jaw position so that both first and second jaws define a grip portion; and
    an actuator configured for opening and closing the second jaw, the actuator being rotationally connected to the main body and comprising an open actuator position and a closed actuator position,
    wherein the actuator and the second jaw are linked by a kinematic chain so that a passage of the actuator from one actuator position to another actuator position causes the second jaw to pass from one jaw position to another jaw position respectively,
    wherein a rotational movement of the actuator is contained in a first plane and a rotational movement of the second jaw is contained in a second plane wherein an orientation of the first plane and an orientation of the second plane are different,
    wherein the actuator is rotationally connected to the main body at a first joint and the second jaw is rotationally connected to the main body at a second joint separated along the main body from the first joint, and
    wherein the actuation of the actuator is linked with the rotational movement of the second jaw relative to the main body so that a gripper of the clamp can be regulated.

2. Bone clamp according to claim 1, wherein the second plane and the first plane has an angle in a range of 60° to 120°.

3. Bone clamp according to claim 1, wherein the second plane and the first plane has an angle in a range of 70° to 110°.

4. Bone clamp according to claim 1, wherein the second plane and the first plane has an angle in a range of 80° to 110°.

5. Bone clamp according to claim 1, wherein the second plane is perpendicular to the first plane.

6. Bone clamp according to claim 1, wherein the kinematic chain is partially housed within the main body, the actuator pivots in a first joint of the main body and the second jaw pivots in a second joint of the main body by means of the rotation of the actuator, the second joint being separated from the first joint.

7. Bone clamp according to claim 1, wherein the kinematic chain comprises:
    a slider; and
    a first and second rod-cranks,
    wherein the kinematic chain is adapted to transform the rotational movement of the actuator to a linear displacement of the slider by means of the first rod-crank rotatably connecting the actuator and the slider, and subsequently to transform the linear displacement of the slider to the rotational movement of the second jaw by means of the second rod-crank rotatably connecting the slider and the second jaw.

8. Bone clamp according to claim 7 wherein in operative mode, the first rod-crank movement is in the first plane and, in operative mode, the second rod-crank movement is in the second plane.

9. Bone clamp according to claim 7, wherein the actuator is connected to a first rod-crank by means of an extension arm extending the actuator to an opposite side of a first joint about which the actuator rotates, so that the opening of the actuator causes the second jaw to open.

10. Bone clamp according to claim 7, wherein the actuator is directly connected to the first rod-crank so that the opening of the actuator causes the second jaw to close.

11. Bone clamp according to claim 1 further comprising an actuator movement regulation mechanism comprising a locked position where the actuator is fixed and a free position where the actuator can rotate.

12. Bone clamp according to claim 11, wherein the actuator movement regulation mechanism is a ratchet mechanism and comprises:
  an arc-shaped rack protruding from the main body and comprising a plurality of teeth; and
  a pawl rotationally connected to the actuator and comprising a tooth that matches those teeth of an arc-shaped rack,
  wherein in the free position of the mechanism, the pawl is configured to rotate with respect to the actuator and to slide through the arc-shaped rack thus allowing the actuator to rotate with respect to the arc-shaped rack, and
  wherein in the locked position, the pawl movement remains blocked so that the actuator remains fixed.

13. Bone clamp according to claim 12, wherein the ratchet mechanism further comprises a spring element attached to the actuator and arranged to apply a force to the pawl thus ensuring a contact of the tooth of the pawl with the teeth of an arc-shaped rack.

14. Bone clamp according to claim 12, wherein the ratchet mechanism further comprises a security handle protruding from the actuator and configured to lock the movement of the pawl in the locked position of the mechanism.

15. Bone clamp according to claim 1 further comprising a kinematic coupling connected to the main body in an end opposite to the first jaw, the kinematic coupling being configured to be coupled to tracking means so that the bone clamp provides an anchor reference.

16. Bone clamp according to claim 15, wherein the kinematic coupling comprises:
  a female portion comprising a ferromagnetic element; and
  a male portion comprising a magnet,
  wherein the ferromagnetic element and the magnet provide a bonding force between both female and male portions.

17. Bone clamp according to claim 1, wherein the first and second jaws each comprise a plurality of spikes such that in the closed jaw position, the spikes of both first and second jaws are facing each other.

18. Surgical clamp comprising:
  a main body comprising at one end a first jaw, the main body and the first jaw forming a single rigid body;
  a second jaw being independent from the main body but rotationally connected to the main body and being opposite of the first jaw, the second jaw comprising an open jaw position and closed jaw position so that both first and second jaws define a grip portion;
  an actuator configured for opening and closing the second jaw the actuator being rotationally connected to the main body and comprising an open actuator position and a closed actuator position;
  a female portion comprising a ferromagnetic element; and
  a male portion comprising a magnet,
  wherein the ferromagnetic element and the magnet provide a bonding force between both female and male portions, and wherein the actuator and the second jaw are linked by a kinematic chain so that a passage of the actuator from one actuator position to another actuator position causes the second jaw to pass from one jaw position to another jaw position respectively, and
  wherein a rotational movement of the actuator is contained in a first plane and the rotational movement of the second jaw is contained in a second plane wherein an orientation of the first plane and an orientation of the second plane are different,
  wherein the actuator is rotationally connected to the main body at a first joint and the second jaw is rotationally connected to the main body at a second joint separated along the main body from the first joint, and
  wherein the actuation of the actuator is linked with the rotational movement of the second jaw relative to the main body so that a gripper of the clamp can be regulated.

19. Surgical clamp according to claim 18, wherein the first and second jaws each comprise a plurality of spikes so that in the closed jaw position, the spikes of both first and second jaws are facing each other.

20. Surgical clamp according to claim 18, wherein the second plane and the first plane has an angle in a range of 60° to 120°.

* * * * *